United States Patent
Tiedge

(10) Patent No.: US 7,510,832 B2
(45) Date of Patent: Mar. 31, 2009

(54) MOLECULAR DIAGNOSIS AND PROGNOSIS OF CARCINOMAS

(75) Inventor: Henri Tiedge, New York, NY (US)

(73) Assignee: The Research Foundation of State University of New York, Albany, NY (US)

(*) Notice: Subject to any disclaimer, the term of this patent is extended or adjusted under 35 U.S.C. 154(b) by 0 days.

(21) Appl. No.: 10/503,782

(22) PCT Filed: Feb. 21, 2003

(86) PCT No.: PCT/US03/05502

§ 371 (c)(1),
(2), (4) Date: Aug. 6, 2004

(87) PCT Pub. No.: WO03/073065

PCT Pub. Date: Sep. 4, 2003

(65) Prior Publication Data

US 2005/0164189 A1    Jul. 28, 2005

Related U.S. Application Data

(60) Provisional application No. 60/359,156, filed on Feb. 22, 2002.

(51) Int. Cl.
*C12Q 1/68* (2006.01)
(52) U.S. Cl. .................................................. 435/6
(58) Field of Classification Search ................ 435/6
See application file for complete search history.

(56) References Cited

U.S. PATENT DOCUMENTS 5,670,318 A    9/1997    Tiedge et al.

FOREIGN PATENT DOCUMENTS

WO    WO 94/28176    12/1994

OTHER PUBLICATIONS

Chen et al (Journal of Pathology, 1997, 183:345-351).*
Tockman et al (Cancer Res., 1992, 52:2711s-2718s).*
Wilson (Encyclopedia of Molecular Biology vol. 3, John Wiley & Sons, 1999, pp. 1903-1908).*
Schwemmle et al (Proceedings of the National Academy of Sciences, USA, 1992, 89:10292-10296).*
Shoker and Sloane (1999, Histopathology, 35:393-400).*
Wilson et al (Encyclopedia of Molecular Biology vol. 3, John Wiley & Sons, 1999, pp. 1903-1908).*
Chen et al. (1997) *Expression of Neural BC200 RNA in Human Tumours*, Journal of Pathology, vol. 183: pp. 345-351.
Elston et al. (1998) *The Breast*, Ch. 17, pp. 365.
Elston et al. (1998) *The Breast*, Ch. 14, pp. 249-28.
Ernster V.L. (1997) "Increases in Ductal Carcinoma In Situ In Relations to Mamography: A Delemma", *J. Nat. Can. In. Mons.* 22:151-156.
Garnick et al., (1998), "Combating Prostate Cancer", *Sci. Am.* 279:75-83.
Gerdes, J., (1990) "Ki-67 and Other Proliferation Markers Useful for Immunohistological Diagnostic and Prognostic Evaluations in Human Malignancies", *Semin. Cancer Biol.* 1:199-206.
Iacoangeli A., et al. (2004) "BC200 RNA in Invasive Breast Cancer" *Carcinogenesis* (25) 11:2125-2133.
Lin, Y. et al. (2001) "Neuronal BC1 RNA: Co-Expression with Growth-Associated Protein-43 Messenger RNA" *Neuroscience* 103(2): 465-479.
Mughal et al., (Apr. 18, 1983) "Serial Plasma Carcinoembryonic Antigen Measurements During Treatment of Metastatic Breast Cancer", *JAMA* 249 (14):1881-1886.
Slamon et al., (Jan. 1987) "Human Breast Cancer: Correlation of Relapse and Survival With Amplification of the HER-2/neu Oncogene", *Science* 235:177-182.
Tidege et al., (1993) "Primary Structure, Neural-Specific Expression, and Dendtritic Location of Human BC200 RNA", *J. Neurosic.* 13 (6):2382-2390.
Watson and Sutcliffe (Sep. 1987) "Primate Brain-Specific Cytoplasmic Transcript of the Alu Repeat Family" *Molecular & Cellular Biology* 7 (9):3324-3327.
Wang, et al., (Dec. 1, 2002) "Dendritic BC1 RNA: Functional Role in Regulation of Translation Initiation", *J. Neurosci*, 22:10232-10241.

* cited by examiner

*Primary Examiner*—Sean E Aeder
(74) *Attorney, Agent, or Firm*—Dilworth & Barrese, LLP

(57) ABSTRACT

The present invention is directed to the use of human BC200 RNA in both the diagnosis and prognosis of carcinomas to determine the presence of a carcinoma and tumor grade, and also to predict the likelihood that a carcinoma will progress to an invasive carcinoma.

3 Claims, No Drawings

MOLECULAR DIAGNOSIS AND PROGNOSIS OF CARCINOMAS

CROSS REFERENCE TO RELATED APPLICATIONS

This application is a national phase application of PCT/US03/05502, having an international filing date of Feb. 21, 2003, which claims priority to U.S. Provisional Application No. 60/359,156, filed Feb. 22, 2002, the contents of which are incorporated by reference herein.

STATEMENT REGARDING FEDERALLY SPONSORED RESEARCH OF DEVELOPMENT

This invention was made with Government support under DOD Grants DAMD 17-96-1-6201 and DAMD 17-02-1-0520. The Government has certain rights in the invention.

BACKGROUND OF THE INVENTION

1. Technical Field

This invention relates to the use of a molecular marker, BC200 RNA, in screening for neoplastic diseases. Methods may be used by which BC200 RNA expression may be monitored and utilized for both the diagnosis and prognosis of carcinomas.

2. Background of Related Art

Progress in the diagnosis and prognosis of cancer has been hampered by the lack of suitable, reliable and sensitive molecular markers. Such indicators are necessary to identify lesions and characterize them, to distinguish benign from malignant tumors, and to be able to determine whether a given non-invasive carcinoma will become invasive in the future.

For example, no reliable molecular marker is currently available that could be used to complement mammography in the detection of breast cancer. This contrasts with prostate cancer, for example, where prostate-specific antigen (PSA) status can be established by simply analyzing a blood sample. PSA is a molecular marker for prostate cancer (reviewed by Gamick et al., "Combating Prostate Cancer", *Sci. Am.* 279: 75-83 (1998)), and although PSA status is not a very reliable tumor indicator (with relatively high false negative and false positive rates), it is routinely used in the clinical diagnosis of prostate malignancies.

Other markers for tumors are also known. For example, carcinoembryonic antigen (CEA) is of prognostic value for colorectal carcinoma; in breast cancer, CEA and CA15-3 are used as postoperative markers (Mughal et al., "Serial Plasma Carcinoembryonic Antigen Measurements During Treatment of Metastatic Breast Cancer", *JAMA* 249:1881-1886 (1983)), but not in preoperative diagnosis. BRCA1/2 status can be used as a risk factor indicator, HER-2/neu (c-erbB-2) status correlates with relapse and survival (Slamon et al., "Human Breast Cancer: Correlation of Relapse and Survival With Amplification of the HER-2/neu Oncogene", *Science* 235: 177-182 (1987)), and Ki-67 is a proliferation marker that is useful in the determination of the growth fraction of a tumor (Gerdes, "Ki-67 and Other Proliferation Markers Useful for Immunohistological Diagnostic and Prognostic Evaluations in Human Malignancies", *Semin. Cancer Biol.* 1:199-206 (1990)). However, these markers are of limited usefulness in tumor detection, diagnosis and prognosis.

BC200 RNA is a 200-nucleotide long, non-translatable RNA that is prevalently expressed in the nervous system of primates, including man. A partial nucleotide sequence of BC200 RNA from monkey brains was first reported by Watson and Sutcliffe, *Molecular & Cellular Biology* 7,3324-3327 (1987). This 138 nucleotide sequence showed substantial homology to the Alu left monomer, a sequence that is repeated many times throughout the human and other primate genomes. The sequence of full-length BC200 RNA was subsequently reported by Tiedge et al., "Primary Structure, Neural-Specific Expression, and Dendritic Location of Human BC200 RNA", *J. Neurosci.* 13, 2382-2390 (1993).

The primary sequence of human BC200 RNA is as follows:

[SEQ ID NO 1]

```
XXCCGGGCGCGGUGGCUCACGCCUGUAAUCCCAGCUCUCAGGGA
GGCUAAGAGGCGGGAGGAUAGCUUGAGCCCAGGAGUUCGAGACC
UGCCUGGGCAAUAUAGCGAGACCCCGUUCUCCAGAAAAAGGAAA
AAAAAAACAAAAGACAAAAAAAAAAUAAGCGUAACUUCCCUCAA
AGCAACAACCCCCCCCCCCUUU
```

Expression of the small neuronal non-coding transcript BC200 RNA, itself a modulator of translation (Wang, et al., "Dendritic BC1 RNA: Functional Role in Regulation of Translation Initiation", J. Neurosci, vol. 22, pages 10232-10241(2002)), is tightly regulated. The RNA is not normally detected at higher than background levels in non-neuronal somatic cells (Tiedge et al., supra). However, the tight neuron-specific control of BC200 RNA expression is deregulated in various tumors, including breast tumors. BC200 RNA is associated with malignancy and is not detectable in normal non-neuronal somatic tissue or in benign tumors such as fibroadenomas of the breast. Lin et al. "Expression of Neural BC200 RNA in Breast Cancer", Era of Hope Proceedings, Vol. 1, p. 122 (Department of Defense, 2000).

U.S. Pat. Nos. 5,670,318 and 5,736,329, the contents of each of which are incorporated by reference herein, disclose the complete sequence of human BC200 RNA and the use of polynucleotide probes which can be used to specifically detect the presence of human BC200 RNA in a tissue sample.

The primary sequence of BC200 RNA can be subdivided into three structural domains. Domain I is nucleotides 1-122 and is substantially homologous to Alu repetitive elements which are found in high copy numbers in primate genomes. However, this region includes two bases not found in Alu or SRP-RNA, i.e., nucleotides at positions 48 and 49, which can be used to develop amplification primers specific to BC200 RNA sequences. Domain II is an A-rich region consisting of nucleotides 123-158. Domain III, consisting of nucleotides 159-200, contains a unique sequence with no homology to other known human sequences which can be used to identify BC200 RNA in tissues.

Oncological pathologists have long recognized that the differing degrees of malignancy of tumors is reflected in their morphological structure. There are three general grades of tumors, low, intermediate and high, with the high grade typically being associated with the most aggressive tumors (Elston et al., *The Breast*, Ch. 17, pp. 365-383, (1998)).

Ductal carcinoma in situ (DCIS) is a common but heterogeneous group of neoplastic diseases. Approximately 25% of DCIS will develop into invasive carcinomas within 15 years if left untreated (Elston et al., *The Breast*, Ch. 14, pp. 249-281, (1998)). However, to date there is no reliable indicator, molecular or otherwise, to predict the invasive potential of a given DCIS. Most women therefore elect to have DCIS removed surgically, which in many instances is unnecessary and amounts to over-treatment (Ernster, "Increases in Ductal Carcinoma In Situ in Relation to Mammography: A Dilemma", *NIH Consensus Development Conference on Breast Cancer Screening for Women Ages* 40-49, pp. 147-151 (NIH, 1997)).

Clearly, a reliable prognostic indicator of cancer, including DCIS, would be most valuable in assisting physicians and patients in making informed treatment decisions.

SUMMARY OF THE INVENTION

The present invention is directed to methods for diagnosing invasive carcinomas and determining the likelihood that a carcinoma which is not yet invasive is likely to become an invasive carcinoma. The present invention is also directed to methods for determining the tumor grade of a sample.

The methods include: obtaining a physiological sample from a human; preparing the test sample such that RNA in the test sample is capable of reacting with a detection reagent possessing a labeling signal; combining the test sample with the detection reagent under conditions that produce a detectable reaction product if human BC200 RNA is present; measuring the amount of detectable reaction product by its labeling signal; comparing the level of labeling signal to a labeling signal from a non-high grade carcinoma control or any other suitable control such as normal tissue that does not express BC200 RNA; and correlating an elevated labeling signal in the test sample with a determination that the carcinoma is of a grade likely to become invasive.

Where the method is utilized for diagnosing an invasive carcinoma, the labeling signal from a test sample is compared to a labeling signal from a non-invasive carcinoma control. An elevated signal in the test sample compared to a non-invasive carcinoma control indicates the presence of an invasive carcinoma in the sample.

Where the method is directed to determining tumor grade, the labeling signal in the test sample is compared correlated with the labeling signal in a non-high grade carcinoma control and/or an intermediate-grade carcinoma control prepared using the same steps as the test sample. A relative same level of labeling signal in the test sample and a low-grade carcinoma control indicates a low-grade carcinoma in the test sample. Where an elevated amount of labeling signal in the test sample is present compared to the amount of labeling signal from a low-grade carcinoma control, at least an intermediate-grade carcinoma in the test sample is indicated. In such a case, the test sample may be compared with an intermediate-grade carcinoma control prepared using the same steps as the test sample. Where an elevated amount of labeling signal in the test sample is present compared to an intermediate-grade carcinoma control, a high grade carcinoma in the test sample is indicated.

In one embodiment, the detection reagent utilized in the methods of the present invention is an oligonucleotide probe capable of hybridizing with human BC200 RNA and RT-PCR is utilized to produce a detectable reaction product if human BC200 RNA is present.

Preferably, the amount of labeling signal is measured by a technique selected from the group consisting of emulsion autoradiography, phosphorimaging, light microscopy, confocal microscopy, multi-photon microscopy, and fluorescence microscopy. Quantitative analysis may be conducted to determine the labeling signal intensity, which may then be utilized in the diagnosis and prognosis of carcinomas.

Preferably, carcinomas and/or tumors diagnosed in accordance with the methods of the present invention may be carcinomas of the breast including, but not limited to, carcinomas in situ, which in turn include ductal carcinoma in situ and lobular carcinoma in situ; infiltrating carcinomas, which in turn include infiltrating ductal carcinomas and infiltrating lobular carcinomas such as tubulo-lobular carcinomas; mucinous carcinomas; and medullary carcinomas. Other carcinomas monitored in accordance with the methods of the present invention include, but are not limited to, tumors of the skin, kidney, parotid gland, lung, bladder and prostate.

DETAILED DESCRIPTION OF THE INVENTION

In accordance with the present invention, it has been surprisingly found that not only may BC200 RNA be used to detect various carcinomas but, in addition, by monitoring BC200 RNA levels, tumor grade may be determined as well as the likelihood that a carcinoma is of a grade likely to become invasive.

Carcinomas which may be monitored and diagnosed in accordance with the present invention are varied and include, but are not limited to, carcinomas of the breast, such as infiltrating mammary carcinomas, e.g., infiltrating ductal carcinomas (IDC) and infiltrating lobular carcinomas (ILC), which in turn include tubulo-lobular carcinomas; carcinomas in situ, e.g., ductal carcinoma in situ (DCIS) and lobular carcinomas in situ (LCIS); mucinous carcinomas; medullary carcinomas; and others. Other carcinomas which may be monitored and diagnosed include, but are not limited to, carcinomas of the skin, kidney, parotid gland, lung, bladder and prostate.

It should be noted that BC200 RNA can not be classified as a proliferation marker, for two reasons. First, of all normal somatic cells, only neurons express BC200 RNA. Most neurons are post-mitotic and do not proliferate. Secondly, proliferating somatic cells, with the exception of cancer cells such as mammary carcinoma cells, do not express BC200 RNA. Thus, BC200 expression is not associated with proliferation per se, but rather with specific malignancies, in particular with invasive potential.

In one embodiment, the present invention provides a prognostic method for determining the likelihood that a carcinoma is of a grade likely to become an invasive carcinoma. This method may also be used in the diagnosis of invasive tumors. This method involves obtaining a physiological test sample from a human, preparing the test sample such that RNA in the test sample is capable of reacting with a detection reagent possessing a labeling signal, combining the test sample with the detection reagent under conditions that produce a detectable reaction product if human BC200 RNA is present, measuring the amount of detectable reaction product by its labeling signal, comparing the amount of labeling signal for the test sample to a labeling signal from a non-high grade carcinoma control prepared using the same steps as the test sample, and correlating an elevated amount of labeling signal in the test sample with a determination that the carcinoma is likely to become invasive.

In another embodiment, the present invention provides a method for determining tumor grade. This method involves obtaining a physiological test sample from a human, preparing the test sample such that RNA in the test sample is capable of reacting with a detection reagent possessing a labeling signal, combining the test sample with the detection reagent under conditions that produce a detectable reaction product if human BC200 RNA is present, measuring the amount of detectable reaction product by its labeling signal, and comparing the amount of labeling signal measured in the test sample to a labeling signal from a non-high grade carcinoma control prepared using the same steps as the test sample. Relatively the same level of labeling signal in the test sample and a low-grade carcinoma control prepared using the same steps as the test sample indicates a low-grade carcinoma in the test sample; an elevated amount of labeling signal in the test sample compared to the amount of labeling signal from a low-grade carcinoma control prepared using the same steps as the test sample indicates at least an intermediate-grade carcinoma in the test sample; and an elevated amount of labeling signal in the test sample compared to an intermediate-grade carcinoma control prepared using the same steps as the test sample indicates a high grade carcinoma in the test sample.

Preferably, the detection reagent utilized in the methods of the present invention is an oligonucleotide probe capable of hybridizing with human BC200 RNA, and RT-PCR is utilized to produce a detectable reaction product if human BC200 RNA is present in a test sample. Most preferably, the detectable reaction product possesses a labeling signal, such as a fluorescent signal.

Examples of oligonucleotide probes which may be used to monitor the level of BC200 RNA in a sample are described in U.S. Pat. Nos. 5,670,318 and 5,736,329. Such probes are complementary to the unique sequences of Domain III of human BC200 RNA, or to its corresponding chromosomal DNA, i.e., complementary to at least a portion of the sequence:

UAAGCGUAAC UUCCCUCAAA GCAACAACCC    [SEQ ID NO 2]

CCCCCCCCCU UU 42

The probes may be linear oligonucleotides containing from about 10 to 60 bases. The length must be sufficient to provide a reasonable degree of specificity such that binding with BC200 RNA will be preferred over binding to other polynucleotides.

As used herein, the term "oligonucleotide probe" refers to either a DNA or an RNA probe.

One probe within the scope of the invention is complementary to the nucleotides 156-185 of BC200 RNA. This 30-nucleotide probe has the sequence:

TTGTTGCTTT GAGGGAAGTT ACGCTTATTT 30 [SEQ ID NO 3]

Another useful probe is a 21-nucleotide probe complementary to nucleotides 158-178, i.e.:

TTTGAGGGAA GTTACGCTTA T 21    [SEQ ID NO 4]

As is apparent, suitable probes may be complementary with the portions of BC200 RNA outside Domain III, provided they are also complementary to a portion (i.e., at least about 10 bases) of the unique Domain III sufficient to provide specificity. Probes may also be complementary to portions of Domain III alone. A second class of probes may also be used which are complementary to a portion of Domain II, spanning nucleotides 146-148. The above probes may be used for detection of BC200 RNA or as amplification primers.

In another aspect of the invention, probes can be utilized which are complementary to, and specifically hybridize with, a portion of the Alu-repetitive sequence spanning the two unique nucleotides at positions 48 and 49 of BC200 RNA or its corresponding DNA. Examples of such probes are:

CCTCTTAGCC TCCCTGAGAG CT 22    [SEQ ID NO 5]

an antisense probe that will bind BC200 RNA and:

CCAGCTCTCA GGGAGGCTAA 20    [SEQ ID NO 6]

a sense probe that will bind to corresponding DNA sequences. These probes can be used for detection or as amplification primers.

The probes utilized in accordance with the present invention can be made by any of a variety of techniques known in the art. For example, RNA probes can be generated by in vitro transcription. In this approach, the desired sequence is first cloned into a suitable transcription vector (e.g., pBluescript). This vector is linearized so that transcription will terminate at a specific location, and RNA is transcribed from such linearized templates, using SP6, T3, or T7 RNA polymerase. The probes can be $^{35}$S- or $^{3}$H-labeled by adding the appropriate radiolabeled precursors to the reaction mixture. Template DNA is then digested with DNase I. RNA probes can be further purified by gel filtration or gel electrophoresis.

Probes can also be made by oligolabeling, although this technique is more suited to longer nucleic acid polymers. In this method, double stranded DNA is first denatured. Random sequence oligonucleotides are then used as primers for the template directed synthesis of DNA. The Klenow fragment of *E. coli* DNA polymerase I is frequently used in this application. Reverse transcriptase can be used if the template is RNA. Labeling of the probe is achieved by incorporation of radiolabeled nucleotides, e.g., [$\alpha$-$^{32}$P]dNTps.

Another approach for generation of probes is nick translation. Double stranded DNA is used in this method. Nicks (gaps in one strand) are introduced by DNase I. *E. coli* DNA polymerase I is used simultaneously to add nucleotide residues to the 3' termini of the DNA at the nick points. Incorporation of radiolabeled precursor nucleotides results in the uniform labeling of the probe. Probes contain both strands.

Single stranded DNA probes can be made from templates derived from bacteriophage M13 or similar vectors. An oligonucleotide primer, complementary to a specific segment of the template, is then used with the Klenow fragment of *E. coli* DNA polymerase I to generate a radiolabeled strand complementary to the template. The probe is purified for example by gel electrophoresis under denaturing conditions.

Oligonucleotides of any desired sequence can also be synthesized chemically. Solid phase methods are routinely used in the automated synthesis of oligonucleotides.

Probes useful in accordance with the present disclosure can be labeled. A variety of enzymes can be used to attach radiolabels (using dNTP precursors) to DNA termini. The 3' termini of double stranded DNA can for example be labeled by using the Klenow fragment of *E. coli* DNA polymerase I. Blunt ended DNA or recessed 3' termini are appropriate substrates. T4 DNA polymerase can also be used to label protruding 3' ends. T4 polynucleotide kinase can be used to transfer a $^{32}$P-phosphate group to the 5' termini of DNA. This reaction is particularly useful to label single stranded oligonucleotides. Probes can also be labeled via PCR labeling in which labeled nucleic acids and/or labeled primers are used in PCR generation of probes from an appropriate clone. See Kelly et al., Genomics 13: 381-388 (1992).

The methods of the present invention utilize oligonucleotide probes like those described above to screen tissue for the presence of BC 200 RNA which, itself, is utilized to diagnose carcinomas and determine whether or not it is likely that a given carcinoma in situ will progress to an invasive carcinoma.

The basic methodology of the screening procedure involves the following steps:
(1) obtaining a physiological sample;
(2) treating the sample to render RNA and/or DNA available for hybridization;
(3) hybridizing the treated sample with a probe specific for Domain III of human BC200 RNA; and
(4) analyzing for the occurrence of hybridization.

Suitable physiological samples include biopsy specimens, such as surgical specimens, blood, and other body fluids including, but not limited to, nipple discharges, sputum, semen, and scrapings.

While the method employed to treat the tissue sample is not critical, provided that nucleic acids in the sample are made available for hybridization, several specific options are worth noting. Direct isolation of RNA by the guanidine thiocyanate method followed by CsCl-density gradient centrifugation may be effective in many cases, particularly for isolation of RNA from biopsy specimens. Where the sample size is small, however, amplification of the RNA may be desirable.

Amplification of the RNA can be achieved by first lysing cells in the sample to render RNA available for hybridization. This can be accomplished by (1) extraction of RNA with guanidinium thiocyanate, followed by centrifugation in cesium chloride; (2) extraction of RNA with guanidine HCl and organic solvents; or (3) extraction of RNA with mild detergents (such as NP-40), combined with proteinase digestion. These and other RNA extraction methods are described in Sambrook et al., Molecular Cloning, A Laboratory Manual, 3d ed., Cold Spring Harbor Laboratory Press (2001). The isolated RNA is converted into cDNA which is then amplified using probes selective for the 3' end of BC200 RNA sequence. (See U.S. Pat. No. 4,683,202, the contents of which are incorporated by reference herein.) cDNA may also be amplified using ligase-based methods (Barany et al., "Genetic Disease Detection and DNA Amplification Using Cloned Thermostable Ligase", *Proc. Nat'l. Acad. Sci. USA* 88, 189-193 (1991)) or isothermal transcription-based methods (Kwoh et al., "Transcription-based Amplification System and Detection of Amplified Human Immunodeficiency Virus Type 1 With a Bead-based Sandwich Hybridization Format", *Proc. Nat'l. Acad. Sci. USA* 86, 1173-1177 (1989)). The amplified DNA can then be detected directly via an appropriate probe.

The hybridization can be carried out using any of the numerous procedures known for assaying for nucleic acids. These include various blot techniques (i.e., dot, Northern, Southern, etc.), and sandwich based techniques such as those described in U.S. Pat. Nos. 4,486,539; 4,751,177; 4,868,105; 4,894,325 and European Patent Publication 0 238 332 (the contents of each of which are incorporated by reference herein). To facilitate detection, the probe may have a label, such as a radiolabel, chemiluminescent label, fluorescent label or chromogenic label, or an immobilization moiety. Probes modified with biotin or digoxygenin, which can serve as either a detectable label or an immobilization moiety, may be particularly useful.

In addition, other techniques such as reverse transcription polymerase chain reaction (RT-PCR) may be utilized to detect BC200 RNA in small samples, such as those obtained by fine needle or core needle biopsies, or those obtained from body fluids such as blood or nipple discharges.

In conventional PCR assays, oligonucleotide primers are designed complementary to the 5' and 3' ends of a DNA or RNA sequence of interest. During thermal cycling, DNA or RNA is heat denatured. The sample is then brought to annealing and extension temperatures in which the primers bind their specific complements and are extended by the addition of nucleotide tri-phosphates by a polymerase, such as Taq polymerase. With repeated thermal cycling, the amount of template DNA or RNA is amplified.

In RT-PCR, such as those using TaqMan® chemistry, an oligonucleotide probe may be designed that is complementary to the sequence region between the primers within the PCR amplicon. The probe may contain a fluorescent reporter dye at its 5' end and a quencher dye at its 3' end. When the probe is intact, its fluorescent emissions are quenched by the phenomena of fluorescent resonance energy transfer (FRET). During thermal cycling, the probe hybridizes to the target DNA or RNA downstream of one of the primers. TaqMan® chemistry relies on the 5' exonuclease activity of Taq polymerase to cleave the fluorescent dye from the probe. As PCR product accumulates, fluorescent signal is increased. By measuring this signal, the amplified product can thus be quantified which allows for the quantitation of RNA present in a sample. In combination with the PCR primers, the probe provides another level of specificity in assays to differentiate and quantify the BC200 RNA.

Different primer pairs may be utilized to amplify BC200 RNA by RT-PCR. The 5' portion of BC200 RNA is similar in sequence to human Alu-J repetitive elements. However, BC200 RNA differs from these elements by four nucleotide differences and two tandem base insertions between positions 35-50. Therefore, in one embodiment 5' primers are designed to target this region. The sixty 3'-most nucleotides (nucleotides 141-200) of BC200 RNA are unique, and have been used successfully as a specific probe in Northern and Southern analyses (Tiedge et al., "Primary Structure, Neural-Specific Expression, and Dendritic Location of Human BC200 RNA", *J. Neurosci.* 13, 2382-2390 (1993)).

Preferably, RT-PCR is conducted to detect BC200 RNA, and its fluorescent signal is utilized to determine the invasive potential of a carcinoma.

Signal intensities may be determined by methods known to those skilled in the art including, but not limited to, emulsion autoradiography, phosphorimaging, light microscopy, confocal microscopy, (e.g. confocal laser scanning microscopy) and multi-photon microscopy. In the case of non-radioactive labeling techniques (e.g., using biotin or digoxygenin), light microscopy or fluorescence microscopy may be used.

The labeling intensity for a given sample may then be compared with a labeling signal from a non-high grade carcinoma control. An elevated labeling signal for a test sample compared to the signal from a non-high grade carcinoma control will result in a determination that a given sample contains a carcinoma that is likely to become invasive. Conversely, a low or equivalent labeling signal compared to the signal from a non-high grade carcinoma control will result in a determination that a given sample is either free of carcinoma or, where the source of the sample is a tumor, possesses a carcinoma that is unlikely to become invasive.

Similarly, the labeling signal of a test sample may be compared to a labeling signal from a non-invasive carcinoma control prepared using the same steps as the test sample. An elevated signal in a test sample compared to the labeling signal from a non-invasive carcinoma control may be used to diagnose an invasive carcinoma. Conversely, a low or equivalent signal compared to the non-invasive carcinoma control will result in a determination that the sample does not contain an invasive carcinoma.

In one embodiment, where autoradiography is used to determine the signal intensity in a test sample, the autoradiographs may be subjected to quantitative analysis, preferably using commercially or publicly available image analysis software such as MetaMorph Software (Universal Imaging Corp., Downingtown, Pa.), or NIH Image Software (NIH, Bethesda, Md.). Confocal and multi-photon microscopy may also be used for quantitative analysis. Hand counting may also be used for quantitative analysis, and was the traditional method prior to the introduction of image analysis software.

The resulting labeling signal or signal intensity of a sample may be expressed as "autoradiographic labeling units" or "ALUs", which are relative units equivalent to the number of silver grains per unit area in the autoradiograph which, in turn, is equivalent to the amount of labeling signal. In one embodiment, where autoradiography is used in conjunction with image analysis software (preferably MetaMorph Software) in the quantitative analysis of the signal intensity of a sample, a test sample possessing a labeling signal of greater than about 1000 ALUs may be used to diagnose a high grade or invasive carcinoma. If a carcinoma is not already invasive, there is a high probability a test sample possessing a labeling signal of greater than about 1000 ALUs contains a carcinoma that will progress to an invasive carcinoma. Conversely, a labeling signal of less than about 1000 ALUs may be used to diagnose a non-invasive carcinoma or a non-high grade carcinoma possessing a low probability the carcinoma will progress to an invasive carcinoma. As ALUs are relative units, a different sampling area or the use of different image analysis software may provide a different number. However, as one skilled in the art would readily recognize, relative units may be utilized to compare a test sample with a control and determine whether or not a sample does, in fact, possess an invasive carcinoma or a carcinoma that is likely to progress to an invasive carcinoma.

Similarly, in another embodiment, the present invention is directed to methods for grading tumors. The labeling intensity for a given tumor sample may be compared with a labeling signal in a low-grade carcinoma control. Where the level of labeling signal in a test sample is relatively the same as the labeling signal of a low-grade tumor control, a low-grade tumor is indicated. However, where an elevated amount of labeling signal in a test sample is present compared to the amount of labeling signal from a low-grade tumor control, at least an intermediate-grade tumor in the test sample is indicated. In such a case, a test sample may then be compared with an intermediate-grade tumor control prepared using the same steps as the test sample. Where an elevated amount of labeling signal in the test sample is present compared to an intermediate-grade tumor control, a high grade tumor in the test sample is indicated. By determining the amount of BC200 RNA present in a tumor, the tumor may be graded and a determination made as to whether or not it is likely the tumor will become invasive.

In one preferred embodiment, the methods of the present invention are used in the diagnosis and prognosis of DCIS. In DCIS, BC200 RNA expression is dependent on tumor grade. Comparative genomic hybridization has shown that the transition from DCIS to invasive carcinoma follows a specific genetic pathway that appears to be associated with differentiation status and grade (Buerger et al., "Comparative Genomic Hybridization of Ductal Carcinoma In Situ of the Breast—Evidence of Multiple Genetic Pathways", 187 J. Pathol. 396-402 (1999); Buerger et al., "Different Genetic Pathways in the Evolution of Invasive Breast Cancer are Associated With Distinct Morphological Subtypes", 189 J. Pathol. 521-526 (1999)).

The probes of the invention may be supplied as part of a kit for screening tissue, such as breast tissue, for BC200 RNA. In addition to the probe or other detection reagent that produces a diagnostic reaction product if BC200 RNA is present, such a kit may include one or more of the following:

(1) a solid support to which the diagnostic reaction product nucleic acids are affixed during the screening procedure;
(2) amplification primers and enzymes for amplification of nucleic acids in a sample;
(3) a labeled reagent that reacts with the diagnostic reaction product to render it detectable; and
(4) solutions effective to lyse the physiological sample to render RNA available for hybridization.

Suitable amplification primers include those identified in the Examples, as well as others which will result in amplification, if present, of Domain III of BC200 RNA, possibly together with portions of Domains II and I. A particularly preferred 5'-amplification primer is one that is complementary to a portion of Domain I of BC200 RNA, or the corresponding cDNA, that includes the unique nucleotides at positions 48 and 49. Suitable enzymes include reverse transcriptase, Taq polymerase, rTth DNA polymerase and RNA polymerase.

In accordance with the present invention, it has been surprisingly discovered that the amounts of BC200 RNA expressed by cancerous tumor cells of the breast correlate with tumor type, grade and stage. Thus, BC200 RNA is expressed at high levels in invasive carcinomas. Accordingly, BC200 RNA is used in accordance with the present invention as a molecular indicator in the diagnosis and prognosis of invasive carcinomas, including carcinomas of the breast. The correlation between BC200 RNA expression levels and tumor grade can be used as a molecular indicator of invasive potential. High BC200 RNA levels in a carcinoma indicate a high likelihood of a future invasive carcinoma in that patient. BC200 RNA expression is therefore a valuable tool to predict tumor progression.

It will be understood that various modifications may be made to the embodiments described herein. Therefore, the above description should not be construed as limiting, but merely as exemplifications of preferred embodiments. For example, while the invention is described principally in terms of using oligonucleotide hybridization probes or RT-PCR to detect BC200 RNA levels in those suffering from carcinoma, such as carcinoma of the breast, it will be appreciated that the beneficial result of screening for neoplastic diseases can be achieved using any detection technique. For example, RNA-specific antibodies to BC200 RNA could be used, e.g., in an ELISA assay, to detect BC200 RNA in tissue samples. See Uchiumi et al., "A Human Autoantibody Specific for a Unique Conserved Region of 28 S Ribosomal RNA Inhibits the Interaction of Elongation Factors 1 alpha and 2 With Ribosomes", *J. Biol. Chem.* 266: 2054-62 (1991). Peptide nucleic acids that hybridize with BC200 RNA may also be used as diagnostic reagents. See Hanvey et al., "Antisense and Antigene Properties of Peptide Nucleic Acids", *Science* 258: 1481-1485 (1992). Similarly, BC200 RNA may be complexed with proteins in vivo to form a ribonucleoprotein ("RNP"). Antibodies specific to BC200 RNA could then be used in an immunoassay detection scheme. Those skilled in the art will envision other modifications within the scope and spirit of the features described herein.

EXAMPLE 1

Amplification of BC200 RNA

The 5' and 3' Domains of BC200 RNA were amplified separately. For amplification of the 5' BC200 RNA sequence, 1 µg total RNA was isolated from human neocortex using the guanidinium thiocyanate method followed by phenol extraction and CsCl centrifugation, and converted into first strand cDNA using the thermostable rTth DNA polymerase (Perkin Elmer Cetus) according to the instructions of the manufacturer. The primer used in this step was:

```
   GTTGTTGCTT TGAGGGAAG 19      [SEQ ID NO 7]
```

The 3' end of the product was then T-tailed using dTTP and terminal transferase (Boehringer Mannheim). The tailed cDNA was PCR-amplified (Frohman et al., *Proc. Nat'l. Acad. Sci. USA* 85: 8998-9002 (1988)) in 30 cycles (denaturation for 30 seconds at 94° C., annealing for 1 minute at 55° C., extension for 2 minutes at 72° C.; initial denaturation was for 4 minutes at 94° C., final extension was for 10 minutes at 72° C.), using the primers:

```
GCCTTCGAAT TCAGCACCGA GGGAAGTTAC    [SEQ ID NO 8]
GCTTA 35
and
GCCTTCGAAT CAGCACCAA AAAAAAAAA     [SEQ ID NO 9]
AAAAA 35
```

The products were further amplified in a second set of 30 cycles (conditions see above), using the adapter primer:

```
   GCCTTCGAAT TCAGCACC 18      [SEQ ID NO 10]
```

After digestion with EcoRI, the PCR-products were cloned into the EcoRI site of λ ZAPII (Stratagene) following the manual of the manufacturer. $10^3$ plaques were screened with an internal oligonucleotide probe:

```
AAAAAAAAA(T/A) (T/G)GCCGGGCGC GGT 23 [SEQ ID NO 11]
``` and 6 positive clones were sequenced.

For amplification of the 3' BC200 RNA sequence, 10 μg total RNA from human neocortex were A-tailed using poly A polymerase (DeChiara et al., "Neural BC1 RNA: cDNA Clones Reveal Nonrepetitive Sequence Content", *Proc. Natl. Acad. Sci. USA* 84, 2624-2628 (1987)). Tailed RNA was then converted into first strand cDNA with reverse transcriptase in the presence of MeHgOH (Invitrogen), using the primer:

```
GCCTTCGAAT TCAGCACCTT TTTTTTTTT    [SEQ ID NO 12]
TTTTT 35
```

This primer, in combination with the primer:

```
GCCTTCGAAT TCAGCACCAA AATAAGCGTA   [SEQ ID NO 13]
ACTTCCC 37
``` was also used for PCR-amplification (see above). Products were cloned into λ ZAPII (see above), and 14 clones that were identified with SEQ ID NO 13 were sequenced using the enzymatic chain termination reaction.

EXAMPLE 2

Production of BC200 RNA Specific Probe

Two types of probes have routinely been used. An oligodeoxynucleotide of the desired sequence was chemically synthesized and purified by chromatography or gel electrophoresis. The oligonucleotide was then radiolabeled by phosphorylation of the 5' end. This was achieved by using the enzyme polynucleotide kinase with $\gamma^{32}$P-labeled ATP. The radiolabeled probe (specific activity: >$10^8$ cpm/μg) was separated from unincorporated label by gel filtration, and the probe was used at a concentration of $10^6$ cpm/ml.

In addition, RNA probes were generated by in vitro transcription. In this approach, the desired sequence was first cloned into a suitable transcription vector (e.g., pBluescript). This vector was then linearized (so that transcription would terminate at a desired location), and RNA was transcribed from such linearized templates, using SP6, T3, or T7 RNA polymerase. $^{35}$S- or $^{3}$H-UTP was present during the transcription reaction, and the resulting probes were thus $^{35}$S- or $^{3}$H-labeled. Template DNA was then digested with DNase I, proteins were phenol-extracted, and the probes were ethanol-precipitated. RNA probes were used for in situ hybridization experiments.

EXAMPLE 3

To capture BC200 RNA from blood (Gillespie et al., "Dissolve and Capture: A Strategy for Analyzing mRNA in Blood", *Nature* 367, 390-391 (1994)), biotinylated 2' O-alkyl oligoribonucleotides (Iribarren et al., "2'-O-Alkyl Oligoribonucleotides as Antisense Probes", *Proc. Natl. Acad. Sci. USA* 87, 7747-7751 (1990); Lamond et al., "Antisense Oligoribonucleotides Made of 2'-O Alkyl RNA: Their Properties and Applications in RNA Biochemistry", *FEBS Lett.* 325, 123-127 (1993)) previously used for the concentration and purification of BC1 RNA and BC200 RNA are used. For the analysis of BC200 RNA in blood from breast cancer patients, RNA is captured onto antisense oligoribonucleotides coupled to a matrix through biotin-streptavidin binding. Following repeated washes, captured BC200 RNA is eluted and amplified by RT-PCR.

PCR cycling parameters such as range of annealing temperatures and number of cycles are determined (12-40 cycles, exponential phase and plateau). This is followed by electrophoresis of PCR samples, filter transfer, and hybridization with probes for BC200 RNA and cyclophilin mRNA.

The most efficient PCR primers are selected and optimal PCR conditions are established to determine the ideal conditions for processing RNA that is obtained from fine needle aspirants and core biopsies. Routine short or one-step protocols are used that will most effectively rid the sample of genomic DNA. To ascertain the value of the optimized RT-PCR procedure, samples of human core biopsy material are tested (1-1.5 mm in diameter, 1.7-1.9 cm length). This amount of tissue is sufficient to analyze the RNA content by both PCR and in situ hybridization, in parallel with conventional histopathological methods.

Because BC200 RNA is short and intronless, a negative control without reverse transcriptase (RT) accompanies every experimental sample. A second, positive control is needed to detect false negatives, in case of degraded RNA or of suboptimal RT reaction. Cyclophilin mRNA is chosen to be the reporter RNA used as an internal gauge for efficiency of first strand synthesis. Previous results show that the cyclophilin mRNA is expressed at the same unvarying levels in normal and tumor tissues alike (Chen et al., "Expression of Neural BC200 RNA in Human Tumors", *J. Pathol.* 183, 345-351 (1997)). The purpose of this control experiment is to monitor the overall efficiency of the entire procedure, as performed on the individual sample.

Cyclophilin mRNA primers are tested not only for efficiency of amplification, but also for lack of interference with the ongoing BC200 RNA amplification. The primer pairs for BC200 RNA and for cyclophilin mRNA are selected to amplify with similar efficiency, in the same or in separate tubes. To test the efficiency of primer pairs, RNA samples are used from normal and tumor tissues that are previously tested by Northern or in situ hybridization, and where the relative signal of BC200 RNA (or cyclophilin mRNA) from sample to sample is known, as suggested by Chen et al., supra.

EXAMPLE 4

Human breast tissue was prepared for evaluation. Tissue was obtained and treated to render RNA and/or DNA available for hybridization by freezing in liquid nitrogen. Samples were cryo-embedded in Tissue-Tek OCT embedding medium (Miles, Elkhart, Ind.), frozen in liquid nitrogen, and stored at −80° C. before being sectioned in a Bright Microtome Cryostat at 10 μm thickness following the procedures set forth in Tiedge, H., "The Use of UV Light as a Cross-linking Agent for Cells and Tissue Sections In in situ Hybridization", *DNA Cell Biol.* 10, 143-147 (1991). Sections were thaw-mounted onto gelatin/poly-L-lysine coated microscope slides and stored at −80° C. until further processing. The samples were then subjected to in situ hybridization with a $^{35}$S-labeled RNA probe specific for Domain III of human BC200 RNA human RNA produced in accordance with Example 2 above. In situ hybridization was performed as described in Tiedge et al., "Primary Structure, Neural-Specific Expression, and Dendritic Location of Human BC200 RNA", *J. Neurosci.* 13, 2382-2390 (1993). The final high-stringency wash was performed in 0.1×SSC, 0.05% sodium pyrophosphate, 14 mM 2-mercaptoethanol at 37° C. as described in Tiedge, H., "The Use of UV Light as a Cross-linking Agent for Cells and Tissue Sections In in situ Hybridization", *DNA Cell Biol.* 10, 143-147 (1991).

Tables 1 and 2 below provide semi-quantitative evaluations of the BC200 RNA signals obtained from these samples of breast tissue. The symbols +/−, +, ++, +++, ++++ reflect increasing levels of RNA detected. The diagnosis, grading and classification of the tissue were independently established by cancer pathologists.

TABLE 1

| Case Number | Diagnosis | Grading | Signal |
| --- | --- | --- | --- |
| 1 | Fibroadenoma | | − |
| 2 | Fibroadenoma | | − |
| 3 | Fibroadenoma | | − |
| 4 | Fibroadenoma | | − |
| 5 | DCIS | Non-high grade | +/− |
| 6 | DCIS | Non-high grade | +/− |
| 7 | DCIS | High grade | + |
| 8 | DCIS | High grade | + |
| 9 | DCIS | High grade | + |
| 10 | DCIS | High grade | ++ |
| 11 | DCIS | High grade | ++ |

TABLE 2

| Case Number | Diagnosis | TNM Classification | Signal |
| --- | --- | --- | --- |
| 12 | Invasive ductal carcinoma (with ductal hyperplasia) | T1c, Nx, Mx, HD 3 | ++ |
| 13 | Mixed-differentiated carcinoma | T1b, Nx, Mx, HD 2 | ++ |
| 14 | Invasive ductal carcinoma | T1c, Nx, Mx, HD 3 | ++ |
| 15 | DCIS (Comedo type) | Tis, N0, Mx, HD 3 | ++ |
| 16 | Invasive lobular carcinoma | T1c, Nx, Mx, HD 2 | +++ |
| 17 | Invasive lobular carcinoma (with papilloma) | T1c, Nx, Mx, HD 2 | +++ |
| 18 | Invasive ductal carcinoma (with DCIS) | T1c, Nx, Mx, HD 2 | +++ |
| 19 | Invasive lobular carcinoma (with LCIS) | T1c, Nx, Mx, HD 2 | +++ |
| 20 | Invasive ductal carcinoma (with DCIS) | T2, Nx, Mx, HD 2 | +++ |
| 21 | Invasive lobular carcinoma (with DCIS) | T3, Nx, Mx, HD 3 | +++ |
| 22 | Invasive ductal carcinoma (with DCIS, Comedo type) | T2, Nx, Mx, HD 2 | +++ |
| 23 | Invasive lobular carcinoma (with fibrocystic mastopathy) | T1c, Nx, Mx, | +++ |
| 24 | Invasive ductal carcinoma | T4a, Nx, M1, HD 3 | ++++ |
| 25 | Tubulobular carcinoma (with DCIS) | T4d, Nx, Mx, HD 2 | ++++ |

TNM Classification is the most widely used means for classifying the extent of cancer spread. TNM classification is based on tumor size, number of involved lymph nodes, and number of distant metastases, also known as the tumor-nodes-metastasis (TNM) system. (X means not established.) This system has been adopted by the International Union against Cancer and the American Joint Committee on Cancer as originally published in the 1992 Manual for Staging of Cancer, 4$^{th}$ ed. (Beahrs, O. H., et al.), pp. 149-154 (Philadelphia, Lippincott 1992).

Signal intensities for the above samples were determined by emulsion autoradiography. In particular, signal intensities were obtained for 3 non-high grade DCIS, 4 high-grade DCIS, 5 normal (i.e. non-tumor) tissue samples, and 5 fibroadenomas. Quantitative analysis of autoradiographic silver grain density was performed using MetaMorph software (Universal Imaging Corp., Downingtown, Pa.). Quantitative imaging results were given in the format mean±standard error mean (s.e.m.) in relative units (ALUs). The average labeling intensity determined for non-high grade DCIS was 408±150 ALUs whereas for high grade DCIS, it was 3262±923 ALUs. Normal (i.e. non-tumor) tissue was scored at 206±57 ALUs. Fibroadenomas possessed an average labeling intensity of 502±120 ALUs. Statistical analysis showed that the high grade DCIS signal differed significantly (P<0.05) from non-high grade DCIS signal as well as from normal tissue signal. The non-high grade DCIS signal did not differ significantly from normal tissue signal (P=0.31). Therefore, the labeling intensity of hybridized BC200 RNA provides a categorical (rather than incremental) marker in determining whether or not a DCIS is of a grade likely to become invasive.

In invasive ductal carcinomas (IDC) (ductal carcinoma NST) and infiltrating lobular carcinomas (ILC) including tubulo-lobular carcinomas, high levels of BC200 RNA expression were also found. Invasive carcinomas had high relative signal intensities of 1800-4000 ALUs, depending on tumor type, grade and stage. These values were significantly different (P<0.05) from normal tissue signal and fibroadenoma signal. Thus, non-high grade invasive ductal carcinoma was scored at 1823±478 ALUs (8 cases), high-grade invasive ductal carcinoma at 2957±810 ALUs (8 cases). Both values were significantly different (P<0.05) from normal tissue signal and fibroadenoma signal.

Based upon the above, in accordance with the present invention a labeling signal of greater than about 1000 ALUs determined by autoradiography as described above may be used to predict a high grade DCIS, which has a high probability that it will progress to an invasive carcinoma. A signal of less than about 1000 ALUs may be used to predict a non-high grade DCIS, which has a low probability that it will progress to an invasive carcinoma. A signal intensity of greater than about 1000 ALUs may also be utilized to diagnose invasive carcinoma such as IDC and ILC.

The foregoing results indicate that BC200 RNA levels may be utilized not only in the diagnosis of invasive carcinoma but also for determining whether or not it is likely a carcinoma will progress to an invasive carcinoma. Moreover, it has been discovered that labeling signals for high grade DCIS are significantly higher than in non-high grade DCIS, and approach labeling intensities typical for, and in fact not distinguishable from, invasive carcinomas.

Therefore, BC200 RNA can also be used as an indicator of tumor grade (low grade vs. intermediate grade vs. high grade) and may be utilized in both the diagnostis of invasive carcinomas and the prognosis of carcinomas not yet invasive.

What is claimed is:

1. A method for determining whether a breast carcinoma has an invasive phenotype comprising:
   a) obtaining a physiological test sample comprising breast carcinoma cells from a human;
   b) preparing the test sample such that RNA in the test sample is capable of binding with a detection reagent possessing a labeling signal;
   c) combining the test sample with the detection reagent under conditions that produce a detectable reaction product if human BC200 RNA is present;
   d) measuring the amount of detectable labeling signal associated with the test sample; and
   e) comparing the amount of labeling signal measured in d) to a labeling signal from a non-invasive non-high grade breast tumor control having less than about 1000 ALU units as measured using an image analysis software prepared using the same steps as the test sample; wherein a test sample having the same or lower level of labeling signal compared to the level of labeling in a non-high grade breast carcinoma control in step e) prepared using the same steps as the test sample indicates a non-high grade breast carcinoma in the test sample that is non-invasive; and wherein a test sample having a greater level of labeling signal compared to the level of labeling in a non-high grade breast carcinoma control in step e) prepared using the same steps as the test sample indicates a high grade breast carcinoma in the test sample that is invasive.

2. The method of claim 1 wherein the detection reagent is an oligonucleotide probe capable of hybridizing with human BC200 RNA.

3. The method of claim 1 wherein RT-PCR is utilized to produce a detectable reaction product if human BC200 RNA is present.

* * * * *

```
                        SEQUENCE LISTING

<160> NUMBER OF SEQ ID NOS: 13

<210> SEQ ID NO 1
<211> LENGTH: 200
<212> TYPE: RNA
<213> ORGANISM: human
<220> FEATURE:
<221> NAME/KEY: misc_feature
<222> LOCATION: (1)..(2)
<223> OTHER INFORMATION: n is a or g or c or u

<400> SEQUENCE: 1
nnccgggcgc gguggcucac gccuguaauc ccagcucuca gggaggcuaa gaggcgggag      60
gauagcuuga gcccaggagu ucgagaccug ccugggcaau auagcgagac cccguucucc     120
agaaaaagga aaaaaaaaaa caaaagacaa aaaaaaaaua agcguaacuu cccucaaagc     180
aacaaccccc ccccccuuu                                                  200

<210> SEQ ID NO 2
<211> LENGTH: 42
<212> TYPE: RNA
<213> ORGANISM: Artificial Sequence
<220> FEATURE:
<223> OTHER INFORMATION: oligonucleotide probe

<400> SEQUENCE: 2
uaagcguaac uucccucaaa gcaacaaccc ccccccccu uu                          42

<210> SEQ ID NO 3
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 3
ttgttgcttt gagggaagtt acgcttattt                                       30

<210> SEQ ID NO 4
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 4
tttgagggaa gttacgctta t                                                21

<210> SEQ ID NO 5
```

-continued

```
<211> LENGTH: 22
<212> TYPE: DNA
<213> ORGANISM: Artificial Sequence
<220> FEATURE:
<223> OTHER INFORMATION: oligonucleotide probe

<400> SEQUENCE: 5
cctcttagcc tccctgagag ct                                              22

<210> SEQ ID NO 6
<211> LENGTH: 20
<212> TYPE: DNA
<213> ORGANISM: Artificial Sequence
<220> FEATURE:
<223> OTHER INFORMATION: oligonucleotide probe

<400> SEQUENCE: 6
ccagctctca gggaggctaa                                                 20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
gttgttgctt tgagggaag                                                  19

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
gccttcgaat tcagcaccga gggaagttac gctta                                35

<210> SEQ ID NO 9
<211> LENGTH: 34
<212> TYPE: DNA
<213> ORGANISM: Artificial Sequence
<220> FEATURE:
<223> OTHER INFORMATION: primer

<400> SEQUENCE: 9
gccttcgaat cagcaccaaa aaaaaaaaa aaaa                                  34

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
gccttcgaat tcagcacc                                                   18

<210> SEQ ID NO 11
<211> LENGTH: 23
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
```

```
<222> LOCATION: (10)..(10)
<223> OTHER INFORMATION: w is a or t
<220> FEATURE:
<221> NAME/KEY: misc_feature
<222> LOCATION: (11)..(11)
<223> OTHER INFORMATION: k is g or t

<400> SEQUENCE: 11
aaaaaaaaaw kgccgggcgc ggt                                              23

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
gccttcgaat tcagcacctt tttttttttt ttttt                                 35

<210> SEQ ID NO 13
<211> LENGTH: 37
<212> TYPE: DNA
<213> ORGANISM: Artificial Sequence
<220> FEATURE:
<223> OTHER INFORMATION: primer

<400> SEQUENCE: 13
gccttcgaat tcagcaccaa aataagcgta acttccc                               37
```